United States Patent [19]

Hermann

[11] Patent Number: 5,098,621

[45] Date of Patent: * Mar. 24, 1992

[54] METHOD OF FORMING A FOAM SUBSTRATE AND MICROPACKAGED ACTIVE INGREDIENT PARTICLE COMPOSITE

[75] Inventor: Paul F. Hermann, Boothbay Harbor, Me.

[73] Assignee: Twin Rivers Engineering, Boothbay, Me.

[*] Notice: The portion of the term of this patent subsequent to Oct. 28, 2003 has been disclaimed.

[21] Appl. No.: 335,899

[22] Filed: Apr. 10, 1989

Related U.S. Application Data

[60] Division of Ser. No. 901,749, Aug. 29, 1986, Pat. No. 4,828,542, and a continuation-in-part of Ser. No. 689,249, Jan. 7, 1985, Pat. No. 4,619,948.

[51] Int. Cl.$^5$ .............................................. B29C 67/22
[52] U.S. Cl. .................................. 264/46.4; 264/46.3; 264/109; 264/112; 264/255
[58] Field of Search ...................... 264/109, 255, 45.3, 264/112, 46.4, 46.5, 46.3, 46.6; 428/905

[56] References Cited

U.S. PATENT DOCUMENTS

| | | | |
|---|---|---|---|
| 2,980,941 | 4/1961 | Miller | 15/104.93 |
| 3,088,158 | 5/1963 | Boyle et al. | 15/104.93 |
| 3,317,433 | 5/1967 | Eichel | |
| 3,394,702 | 7/1968 | Heimlich et al. | 604/1 |
| 3,418,656 | 12/1968 | Vassiliades | |
| 3,585,265 | 6/1971 | Motsavage et al. | 264/255 |
| 3,619,842 | 11/1971 | Maierson | 15/104.93 |
| 3,660,321 | 5/1972 | Praetzel et al. | 106/18.18 |
| 3,660,421 | 5/1972 | Praetzel et al. | |
| 3,686,701 | 8/1972 | Charle et al. | 15/104.93 |
| 3,912,665 | 10/1975 | Spitzer et al. | 604/289 |
| 3,968,060 | 7/1976 | Vincent et al. | 264/279.1 |
| 4,138,356 | 2/1979 | Vincent et al. | 106/18.15 |
| 4,182,649 | 1/1980 | Isgur et al. | 428/311.7 |
| 4,226,944 | 10/1980 | Stone et al. | 428/905 |
| 4,254,179 | 3/1981 | Carson, III, et al. | 427/294 |
| 4,309,509 | 1/1982 | Wood | 521/132 |
| 4,349,494 | 9/1982 | Fulmer | 264/46.4 |
| 4,428,983 | 1/1984 | Nehen et al. | 427/213.34 |
| 4,514,461 | 4/1985 | Woo | 428/905 |
| 4,517,308 | 5/1985 | Ehlenz et al. | 428/905 |
| 4,548,954 | 10/1985 | Smith et al. | 521/52 |
| 4,550,126 | 1/1985 | Lorenz | |
| 4,576,771 | 3/1986 | Scholl et al. | 264/109 |
| 4,619,948 | 10/1986 | Kennedy et al. | 264/45.3 |
| 4,654,256 | 3/1987 | Doree et al. | 428/905 |
| 4,661,388 | 4/1987 | Charbonneau | |
| 4,882,112 | 11/1989 | Maki et al. | 264/109 |

FOREIGN PATENT DOCUMENTS

| | | | |
|---|---|---|---|
| 2055019 | 5/1972 | Fed. Rep. of Germany | 604/289 |
| 52-006755 | 2/1977 | Japan | 264/46.4 |

Primary Examiner—Robert A. Dawson
Assistant Examiner—Allan R. Kuhns
Attorney, Agent, or Firm—Daniel H. Kane

[57] ABSTRACT

A new composite material of an open foam substrate and bonded micropackaged active ingredient particles is generated by foam polymerization of a prepolymer phase and an aqueous phase. The foam substrate is an open cell foam for dispensing active ingredient liquids or solids released from the particles. The particles of micropackaged active ingredient liquids or solids are formed with frangible containment walls for breaking and releasing the active ingredient in response to defined stress. The aqueous phase is a pourable and flowable slurry mixture of an aqueous liquid carrier such as water, micropackaged active ingredient particles in the range of 1%-60% by weight of the aqueous phase, and surfactant wetting agent for adjusting the surface tension of the aqueous phase to produce an open cell foam upon polymerization with the prepolymer phase. The prepolymer phase is a hydrophilic polyurethane prepolymer receptive to the aqueous phase for foam polymerization upon mixing. The aqueous phase and prepolymer phase are generally mixed together in a ratio by weight of aqueous phase to prepolymer phase in a range of at least approximately 0.02/1 or greater and preferably 1/1 or greater. Upon foam polymerization, the active ingredient particles are distributed over and intimately bonded to the surfaces of the open foam substrate. The micropackaged particles may constitute any of the available microcontainment systems including microencapsulation system microcapsules and entrapment system microlattices.

5 Claims, 1 Drawing Sheet

METHOD OF FORMING A FOAM SUBSTRATE AND MICROPACKAGED ACTIVE INGREDIENT PARTICLE COMPOSITE

CROSS REFERENCE TO RELATED PATENTS AND PATENT APPLICATIONS

This patent application is a division of U.S. patent application Ser. No. 901,749 filed Aug. 29, 1986, now U.S. Pat. No. 4,828,542 issued May 9, 1989 for FOAM SUBSTRATE AND MICROPACKAGED ACTIVE INGREDIENT PARTICLE COMPOSITE DISPENSING MATERIALS. The present patent application is in turn a continuation-in-part (CIP) of U.S. patent application Ser. No. 689,249, filed Jan. 7, 1985, which patent application is incorporated herein by reference and is now U.S. Pat. No. 4,619,948, issued Oct. 28, 1986 for COMPOSITE ACTIVE FILTER MATERIAL. All the related patents and patent applications are assigned to a common assignee and during the time the respective claimed inventions were made, they were subject to an obligation of assignment to the common assignee.

TECHNICAL FIELD

This invention relates to new dispensing and applicator materials for storing, protecting, selectively releasing, and applying active functional fluids, liquids and solids such as adhesives, cosmetics, pharmaceuticals, flavors, fragrances, colors, inks, liquid crystals, oils, waxes, solvents, resins, fire extinguishants and other chemicals. In particular, the invention provides flexible foam substrate and micropackaged active liquid or active ingredient particle composites for selectively releasing and dispensing active ingredients in response to defined stresses or other selected parameters.

BACKGROUND ART

Two major types of micropackaging or microcontainment systems have been developed for packaging and containing active liquids, fluids, and solids in the form of free-flowing beads, particles, or powders. In microencapsulation, small droplets of the active or functional liquid or solid are coated with a continuous film of polymeric material. Microencapsulation is accomplished by a coacervation process. The microcapsule wall-forming liquid polymer or coating referred to as the coacervate is deposited on droplets or particles of the active liquid or functional ingredient which are in turn dispersed in a liquid vehicle or carrier. The wall coating forms during controlled physical mixing of the liquid vehicle, functional ingredient, and coating material or coacervate. The liquid coating material is solidified while the temperature of the liquid carrier is lowered at a specific pH. The process of microencapsulation and formation of microcapsule systems is further described in the *Encyclopedia of Chemical Technology*, Vol. 13, J. A. Herbig, "Microencapsulation", pp. 436–456, John Wiley & Sons, Inc., 2nd edition, 1967, and various United States patents including U.S. Pat. No. 2,969,330, U.S. Pat. No. 3,137,631, U.S. Pat. No. 3,341,466, U.S. Pat. No. 3,516,943 and U.S. Pat. No. 3,415,758.

In entrapment systems, the active liquid, ingredient, or functional material is contained by sorption within a microscopic polymeric matrix or lattice. The polymer lattice containment results in conversion, for example, of liquids, waxes, or solids into free-flowing particles.

Such micropackaging and microcontainment systems are applicable for storage and protection of active ingredients both liquid and solid, particularly where volatilization otherwise reduces the life or changes the character of the functional material. Micropackaging by encapsulation or entrapment protects the active liquids or solids from deterioration and exposure to air or even light, and increases longevity. For example, micropackaging enhances and improves the fidelity and longevity of emollients, fragrances, and oils. The micropackaging can be designed to provide slow release of a controlled ingredient, long-lasting continuous release by diffusion, or other sustained release patterns.

The micropackaging containment walls of the microcapsules or entrapping lattices may be constructed of a variety of materials to impart a variety of wall characteristics, elastic, rigid, fragile, or tough. Generally the microcontainment walls are sufficiently fragile or frangible to break in response to desired stresses and release the active ingredient or functional liquid or solid. For example, the container walls are typically designed to break in response to a desired level of rubbing or abrading, heating, light exposure, biodegradation, dissolving of the wall, diffusion, pH change, etc.

Polymer entrapment systems are available from Wickhen Products, Inc., Big Pond Road, Huguenot, N.Y., 12746, under the trademark POLYTRAP ™. Typical polymer entrapment particles range in particle size from less than 45 microns to, for example, 3,000 microns, that is from powders to beads. The characteristics of the entrapment materials may be varied according to the lattice wall copolymers and the ratio or percentage of copolymers comprising the particles.

Microencapsulation systems are available from, for example, QMAX Technology Group, P.O. Box 1509, 125 Bacon Street, Dayton, Ohio, 45402, for a variety of products. For example, microcapsules containing minute liquid droplets of essential fragrance oils are available, referred to as "microencapsulated fragrances". Microencapsulated inks and coatings are available for printing and advertising purposes. A variety of cosmetic products are also microencapsulated for various applications. Custom order coacervation microencapsulation techniques are available for any active ingredient on a task basis.

Typical microcapsule size range may be, for example, 40 to 100 microns, though particle size can be controlled from 5 microns to 5,000 microns. The encapsulation coacervate may be typically gelatin, PVA, or urea formaldehyde according to the application. The gelatin encapsulation systems are used for food additives and approved by the FDA.

U.S. Pat. No. 4,514,461 describes a method for producing a fragrance impregnated fabric by mechanically spraying fragrance microcapsules in combination with a liquid binder into the fabric. The fabric is then passed between heated rollers to insure deep and uniform penetration of the microcapsules into the interstices of the fabric. The fabric is either woven or nonwoven and the microcapsules are sufficiently fragile or frangible to break upon rubbing with normal hand pressure to liberate a fragrance or disinfectant. A deodorizer fabric is therefore provided for a variety of applications, such as medical supplies, etc. In U.S. Pat. No. 4,254,179 a method is described for impregnating a porous foam product with microencapsulated fragrance by depositing the microcapsules on one surface of the foam, supplying heat to the foam, and applying a vacuum to the opposite surface of the foam. The microcapsules are thus mechanically forced and distributed through the foam substrate.

A disadvantage of the prior art methods of distributing microencapsulated and micropackaged active ingredient particles through a fabric or foam substrate or matrix is that the forceful mechanical handling of the frangible microcapsules and lattices results in mechanical breakage with premature release of the active liquids or solids. However, U.S. Pat. No. 4,254,179 teaches that the mechanical loss accompanying the mechanical methods is superior to the addition of microcapsules during manufacture of the foam sheet or log because most of the microcapsules otherwise rupture due to the heat and pressure created in processing the foam, immediately liberating and losing much of the fragrance. A further disadvantage of the prior art mechanical methods of distributing micropackaged particles in fabric and foam substrates is that bonding is not assured and particles may be lost in handling.

OBJECTS OF THE INVENTION

It is therefore an object of the present invention to provide a new dispensing material for storing, applying, releasing, and dispensing active ingredient liquids and solids from micropackaged particles such as microcapsules and polymer lattices.

Another object of the invention is to provide a composite dispensing material with intimate bonding between micropackaged active ingredient particles and a foam substrate so that particles are not lost.

A further object of the invention is to provide a new method for producing a composite material of open foam substrate and micropackaged active ingredient particles in which particles are not ruptured or lost during intimate bonding between the particles and substrate.

The invention contemplates composite dispensing materials applicable to and incorporating a fabric skeleton or matrix either woven or nonwoven for a variety of applications. The invention also intends to provide new applicators utilizing the composite dispensing material.

DISCLOSURE OF THE INVENTION

In order to accomplish these results the invention provides a new composite material of an open foam substrate and bonded packaged active ingredient particles generated by foam polymerization of a prepolymer phase and an aqueous phase. The foam substrate is an open cell foam for dispensing active ingredient liquids or solids released from the particles. The particles of micropackaged active ingredient liquids or solids are formed with frangible containment walls for breaking and releasing the active ingredient in response to defined stress.

The aqueous phase is a pourable and flowable slurry mixture of an aqueous liquid carrier such as water, micropackaged active ingredient particles in the range of 1%-60% by weight of the aqueous phase, and surfactant wetting agent for adjusting the surface tension of the aqueous phase to produce an open cell foam upon polymerization with the prepolymer phase. The prepolymer phase is a hydrophilic polyurethane prepolymer receptive to the aqueous phase for foam polymerization upon mixing. The aqueous phase and prepolymer phase are generally mixed together in a ratio by weight of aqueous phase to prepolymer phase in a range of at least approximately 0.2/1 or greater and preferably 1/1 or greater.

A feature and advantage of the invention is that upon foam polymerization, the active ingredient particles are distributed over and intimately bonded to the surfaces of the open foam substrate. According to a preferred example, the aqueous phase is formulated so that the open foam substrate is a reticulated foam with the micropackaged active ingredient particles distributed over and bonded to the webs of the reticulated foam. Furthermore, the micropackaged active ingredient particles are distributed and intimately bonded throughout the foam substrate without the disadvantages of mechanical handling and abrasion and without premature release of the active ingredient.

The micropackaged particles may constitute any of the available microcontainment systems including microencapsulation system microcapsules and entrapment system microlattices. The particle sizes may range from powder size, for example in the range of 1 to 5 microns, to granular and bead sizes from 2,000 to 5,000 microns. A preferred size range of 400 to 1000 microns is used in a variety of applications. The particle size range of 400 to 1,000 microns affords the advantage of apparently invisible or small size while imparting the sensible or tactile feel of breaking and releasing in response to pressure or abrasion.

The resulting composite material of foam substrate and intimately bonded microcontainment particles is formed with the particles of beads composing in the range of 1%-80% by weight of the composite material. The range of percentage composition of micropackaged active ingredient particles determines the rate and volume of "expression" of active ingredient upon application of pressure, abrasion or other environmental eliciting parameter to the composite. At the lower density end of the range, for example several percent by weight of particles, the composite foam substrate expresses only a trace of fluid or other active ingredient upon compression, abrasion or other selected stress while at the higher end of the range approaching 80% a visible flow of liquid or other active ingredient is expressed by the composite dispensing material.

The invention contemplates application of the composite dispensing material for storing, protecting and selectively releasing and dispensing a variety of active or functional liquids, solids and other components collectively referred to herein as "active ingredients". Micropackaged active ingredients for use in the foam substrate composite dispensing materials include fragrances for perfume samplers, air fresheners and drawer liners; insect repellants for moth balls and flea and tick repellants; safety materials such as vaporizable liquid fire extinguishing agents; agricultural chemicals including insecticides, fungicides and pheromones; cleaners and disinfectants including cleaning agents, waxes, solvents and disinfectants; personal care products including skin lotions, hair care, sun screen, mouth wash, vitamins A and E, antiperspirants and contraceptives; medicants such as Benzocaine TM, transdermal drugs, analgesics, allergy bacteria, methyl salicylate, nitroglycerin, Lidocaine TM; adhesives including two component epoxy glues and cyanocrylate superglues; and biological pharmaceuticals such as insulin, interferon, albumin, hormones, monoclonal antibodies, activators, and other biological factors.

By way of a particular example a composite dispensing material according to the invention may be prepared with micropackaged vaporizing liquid fire extinguishing agent such as Halon TM or Halonite TM extinguishant available from ASP International, Inc., American Safety Products Division, 631 Mimosa Drive Northwest, Cleveland, Tenn., 37320. Such bromotrifluoromethane and bromochlorodifluoromethane extinguishants produce a reaction which chemically interrupts the combustion process. The extinguishant is released from micropackages such as the microcapsules at a design temperature for extinguishing flame and retarding propagation of a fire. Foam substrate micropackaged extinguishant particle composites may be manufactured according to the invention in sheet stock of desired thickness as a liner in critical areas such as engine compartments, stove vents, and other fire hazard areas. The sheets are designed to provide release of extinguishants at design temperatures in effective volume quantities.

According to another example, a microencapsulated anaesthetizing drug such as Benzocaine TM is incorporated in the foam substrate composite dispensing material in sheets. Die cut sizes of the foam sheet may be used by a dentist along the gum line of a patient for slow release to anaesthetize an area for dental work. Slow release may be activated upon use by the dentist, for example, by pressure, etc.

The invention provides improved methods and materials for dispensing single component adhesives such as cyanoacrylic superglues. In many applications, the surfaces to be bonded are not closely fitted for successful utilization of superglues. According to the invention a foam sheet composite dispensing material of bonded foam substrate and micropackaged adhesive microcapsules is placed between the two surfaces filling surface irregularities between the surfaces to be glued and dispensing the adhesive for example in response to pressure between the two surfaces. An adhesive bond laminate results. The invention is also useful for two component glue systems such as epoxy resin glue systems with separate micropackages or microcapsules of the epoxy glue and hardener distributed through the foam substrate of the composite dispensing material.

In another embodiment the composite dispensing material incorporates a fabric skeleton or matrix impregnated with the foam substrate and interpenetrating the foam substrate. The fabric skeleton or matrix is preferably a nonwoven material which may be of desired contour. The open foam substrate bonds to fibers and fills the interstices of the nonwoven fabric skeleton or matrix while the micropackaged active liquid or active ingredient particles are distributed over and intimately bonded to the surfaces of the open foam substrate as described above.

The method of producing the new dispensing material includes the steps of preparing an aqueous phase in the form of a pourable or flowable slurry mixture by mixing an aqueous liquid carrier such as water and micropackaged active ingredient particles in the range of 1%–60% by weight of the aqueous phase. Microencapsulated products are conveniently supplied dispersed in de-ionized water. The water carrier protects the beads or microcapsules during transport and handling. A surfactant wetting agent is also mixed in the aqueous phase for adjusting the surface tension of the aqueous phase to produce open cell foam upon polymerization with the prepolymer phase. An oil soluablizer may also be included in the aqueous phase for imparting lipophilic characteristics. Lipophilic characteristics for the resulting composite dispensing material is advantageous where the active ingredient or functional liquid is an oil and the substrate foam is able to absorb the oil upon release from the particles.

The method further includes mixing the aqueous phase with a prepolymer phase in ratio by weight of aqueous phase to prepolymer phase in the range of at least approximately 0.02/1 or greater and preferably 1/1 or greater and foam polymerizing the aqueous phase and prepolymer phase resulting in the open foam substrate and micropackage particle composite with the particles distributed over and bonded to the surfaces of the open foam substrate. Sufficient excess water is included in the aqueous phase for cooling the foam polymerization reaction of the aqueous phase and prepolymer phase and for limiting the reaction temperature so that it does not exceed 130° F. (54° C.).

A feature and advantage of the method of the invention is that the mixing of the aqueous dispersion of microcapsule beads or polymer lattices with the hydrophilic urethane prepolymer does not destroy the integrity of the micropackages or microcontainment systems. Conventionally urethane foam polymerization creates exothermic temperatures in excess of the rupture temperature of the microcapsules or polymer lattices. Foam system exothermic reactions can generate temperatures which destroy the containment walls or volatilize the active ingredient of the microcapsules or micropackages. 180°–210° F. (82°–99° C.) is generally the heat rupture limit for such microcontainment systems. According to the present invention the exothermic heat is controlled and the temperature of the reaction limited so that at most it does not exceed 130° F. (54° C.), generally it does not exceed 120° F. (49° C.), and normally it does not even exceed a temperature range of 100°–110° F. (38°–43° C.) for a reaction starting at room temperature.

Finally, excess moisture is evaporated using for example oven drying of the foam to remove residual water. A feature and advantage of the composite material structure is the protection afforded to the beads by the foam substrate during heat drying. The foam substrate also protects the microcapsule beads or other micropackages from premature rupture and release of active ingredients during handling and mechanical impacts. On the other hand, a firm squeeze or compression of the foam releases the micropackaged ingredient, or the calculated application of other stress designed to break the containment walls releases the ingredient. The microcapsules or other micropackages can be successfully complexed with the foam substrate according to this method in sizes ranging from 5 microns to 5,000 microns (0.0002 to 0.200 inches).

Incorporation of nonwoven fabric or other fabric skeleton or matrix in the composite dispensing material is useful in a variety of applications including scrubbing, abrasive and cosmetic products. For producing such three-component dispensing materials and applicators the invention provides the method of mixing the aqueous phase and prepolymer phase and dispensing the flowable mixture on a fabric material skeleton or matrix, impregnating the skeleton or matrix with the mixed aqueous phase and prepolymer phase, and passing the impregnated fabric skeleton or matrix through a pair or rollers or other compressing elements for distributing the aqueous phase and prepolymer phase mixture throughout the skeleton or matrix and adjusting the density of the mixture. Upon foam polymerization the fabric skeleton or matrix is impregnated with the open foam substrate and interpenetrates the open foam substrate. The foam substrate fills the interstices of the fabric skeleton or matrix with defined density, bonding to the nonwoven fibers, while the micropackaged active ingredient particles are distributed over and bonded to the surfaces of the open foam substrate. Such a skeleton or matrix gives added strength to the dispensing material or applicating material for scrubbing, abrasive, or special purpose cosmetic applications.

In the preferred forms of the method the aqueous phase and prepolymer phase are mixed together in ratio by weight of aqueous phase to prepolymer phase in the range of at least approximately 0.02/1 or greater but preferably in the range of 1/1 to 12/1 and within that range the preferred range of 1/1 to 8/1. At the ratio of 12/1 aqueous phase to prepolymer phase the resulting composite dispensing material is less cohesive but usable, and abrades away like an eraser. At the ratio of 8/1 the composite material achieves desired characteristics of cohesive structure. At the intermediate ratio, for example of 4/1, the resulting foam substrate composite gives desired softness for example for applying to the skin and cosmetic applications. At the lower ratio of 1/1 a tougher foam substrate is produced for heavier duty applications. The microcontainment walls or shells of the micropackages such as microcapsules containing the active ingredient may be formed by the process of coacervation layering using a variety of coacervates including for example gelatin, waxes, polyethylene, polypropylene, urea-formaldehyde, polyamides, ethocel, and polymeric food grade substances. The coacervate may be selected to provide protection against a number of environmental effects including sunlight, photosensitization, microbiological contamination, chemical changes, exposure to the microenvironment, etc., and to respond to any of a number of defined environmental stresses for breaking or rupturing the microcontainment walls or shells and releasing the active solid or liquid ingredient contained by the micropackaging. Thus, the microcapsules, microballoons or beads may be designed, constructed, and arranged to provide the controlled or continuous release of the variety of active ingredients contemplated by the invention into the composite dispensing materials and applicators.

For oil based applications where the active ingredient or functional fluid is an oil, it is advantageous to generate the composite dispensing material according to the invention with a lipophilic substrate foam. The relative hydrophilicity (water absorptivity) or lipophilicity (oil absorptivity) can be designed or selected for the resulting foam substrate by the addition of selective surfactants or addition of primary alcohols according to the procedures of polyurethane chemistry as described for example in U.S. Pat. No. 4,230,566 for "Foamaceous Hydrocarbon Adsorption Medium And Method And System For Making Same" and U.S. Pat. No. 3,793,241 for a "Dimensionally Stable Hydrophilic Foam And Method Of Preparing Same". By way of example, the incorporation of silicone oil surfactant in the aqueous phase results in a lipophilic foam capable of reabsorbing oils released or expressed from microcapsules or other micropackaged particles after squeezing. The addition of an oil soluablizer additionally permits oil and water to be mixed together in the composite dispensing material.

For maintaining low exothermic heat and low temperature levels during polymerization of the aqueous phase with the prepolymer phase, the invention contemplates according to the preferred method the use of a low exothermic heat generating prepolymer such as TREPOL TM isocyanate capped polyol polyurethane prepolymer available from Twin Rivers Engineering, Route 96, East Boothbay, Me., 04544. TREPOL TM prepolymer is a polyether urethane prepolymer of toluene diisocyanate terminated or capped polyethylene glycol with less than 6% available unreacted NCO groups and with an isocyanate functionality less than 2. A feature and advantage of the TREPOL TM type prepolymer characterized by low density of available NCO reactive sites and isocyanate functionality less than 2 accompanied by only small amounts of monomer or low molecular weight components is that the resulting polymerization with the aqueous phase generates lower exothermic heat permitting limitation of the reaction temperature to the range of for example 120° F. (49° C.) and lower. In any event the reaction temperature remains below 130° F. (54° C.) and normally does not even exceed 100°–110° F. (38°–43° C.) for a reaction starting at room temperature. A further advantage of the TREPOL TM prepolymer is that the high water content produces a prepolymer of greater specific heat for more effective dissipation of exothermic heat during reaction. The resulting open foam substrate generated by reaction with the prepolymer with lower density available NCO sites is also characterized by lower toxicity.

The method of the present invention for producing the composite dispensing materials incorporates excess water in the foam polymerization reaction of the aqueous phase with the prepolymer phase. Excess water affords a number of advantages. First, the excess water permits carrying a greater load of microcapsules, polymeric lattices or other micropackages in pourable form into the foam polymerization reaction for greater density of micropackaged active ingredient particles in the resulting composite dispensing material. Second, the pourability and flowability of the aqueous phase and mixture of the aqueous and prepolymer phases permits automation of the composite dispensing material production using metering and mixing machinery and facilitates deposition and permeation of the mixed flow through non-woven material fibers, etc. Third, the excess water helps to dissipate exothermic heat and limit the temperature of the reaction. Fourth, the excess water assures that all available NCO sites are consumed or reacted eliminating toxicity of the resulting composite material.

The method of the present invention is also applicable however with polyurethane prepolymers such as HYPOL TM polyisocyanate capped polyoxyethylene polyol prepolymers having a reaction functionality or isocyanate functionality greater than 2 available from W. R. Grace & Company of New York. Such prepolymers contain more than two reactive isocyanate sites or NCO groups per average molecule with 6%–20% of the unreacted NCO groups available. Such hydrophilic urethane prepolymer compositions and methods of preparation are further described by J. H. Saunders and K. C. Frisch in *Polyurethanes Chemistry and Technology*, Interscience Publishers, John Wiley & Sons, New York, Vol. XVI, Part 2, High Polymer Series, "Foam Systems", pp. 7–26 and "Procedures For the Preparation Of Prepolymers", p. 26 et seq.; the Wolfe U.S. Pat. No.

2,993,013 for "Cellular Polyurethane And Method Of Preparing Same"; the Kistner U.S. Pat. No. 3,805,532; the Wood et al. U.S. Pat. No. 4,137,200 for "Crosslinked Hydrophilic Foams And Method"; and U.S. Pat. No. 4,209,605 for "Process For Producing Shaped Polyurethane Hydrogel Articles". A variety of related formulations are also described in applicant's related co-pending U.S. patent application Ser. No. 689,249, filed Jan. 7, 1985, now U.S. Pat. No. 4,619,948 for "Composite Active Filter Material".

The invention contemplates a particular implementation of the composite foam substrate dispensing material for applicators and daubers such as ear daubers and tips having a handle and molded daubing head. According to this embodiment of the invention, the micropackaged active ingredient particles are not first incorporated in the aqueous phase. Rather, the microcapsules, polymer lattices or other micropackages are spread on the surface of the mold for the applicator head which may be for example a small semi-spherical bowl for producing a rounded spherical tip. The aqueous phase minus the active ingredient particles and prepolymer phase are mixed in suitable proportions and dispensed into the mold and over the surface of the mold for foam polymerization incorporating the beads on the surface of the mold into the surface region of the foam substrate. The applicator handle may be as simple as a paper stick inserted in the mold and bonded in the resulting open foam head for dauber and applicator uses. A variety of active ingredients or functional liquids or solids may be incorporated in the microcapsules bonded over the surface of the applicator head for release upon breaking the microcontainment walls by daubing, pressure, abrasion, etc. For example, the applicators may be used for applying cosmetics, coloring and pigmenting, application of antiseptics or medical ingredients, cleaning, etc.

In a related application the micropackaged active ingredient particles or capsules are distributed and applied over the surface of release paper, a paper treated with release agents such as silicone or wax. The aqueous phase is prepared without incorporation of the prepackaged particles and after mixing the aqueous phase and prepolymer phase the mixture is spread over and on the release paper and layer of beads across the surface of the release paper. The sheet of composite dispensing material is then removed with active ingredient particles or beads embedded and bonded in to the surface of the foam sheet.

The invention contemplates a number of additional novel applications of the composite dispensing material including instant casts and medical dressings using gauze or a nonwoven skeleton matrix impregnated with the composite dispensing material with active ingredient particles for releasing setting agents for the casts or medications for the dressings. Air freshener pads can be produced from the composite dispensing materials for slow release of air freshener active ingredients from the particles. Breath fresheners and flavor applications may utilize the composite dispensing material incorporating larger size particles up to, for example, ⅛" (0.3 cm) diameter beads.

A variety of other novel applications incorporate the nonwoven skeleton or matrix impregnated with the foam substrate and interpenetrating the foam substrate. Active ingredient particles bonded and distributed over the surfaces of foam substrate may incorporate appropriate active ingredients for example for pre-shaving pads or other abrasive applications. Patch kits for boats and autos may incorporate two-part epoxy or polyester resin bonding systems including the resin and hardener. Both components of such two-part glue systems may be encapsulated or only one component may be encapsulated with the other component absorbed within and generally available over the surfaces of the foam substrate.

Cosmetic applications of the invention include pressed powders such as eyeshadow and related color, shade, and pigment applications; lipstick comprising encapsulated active lipstick ingredients bonded and distributed through a foam substrate carrier applicator; nail polish entrapped in a foam nib; bath oil encapsulated or entrapped in microcontainers bonded in a foam hand-held applicator, etc.

The composite dispensing material with embedded skeleton or matrix, for example of nonwoven fabric can be used in a variety of scrubbing and cleaning applications. For example, a nonwoven polyester fiber or skeleton or matrix can impart scrubber characteristics to the composite dispensing material containing, for example, prepackaged PINE-SOL TM active ingredient particles for release of cleaning agents upon scrubbing and application of pressure.

Other objects, features, and advantages of the invention are apparent in the following specification and accompanying drawings.

DESCRIPTION OF PREFERRED EXAMPLE EMBODIMENTS AND BEST MODE OF THE INVENTION

Figure 1:
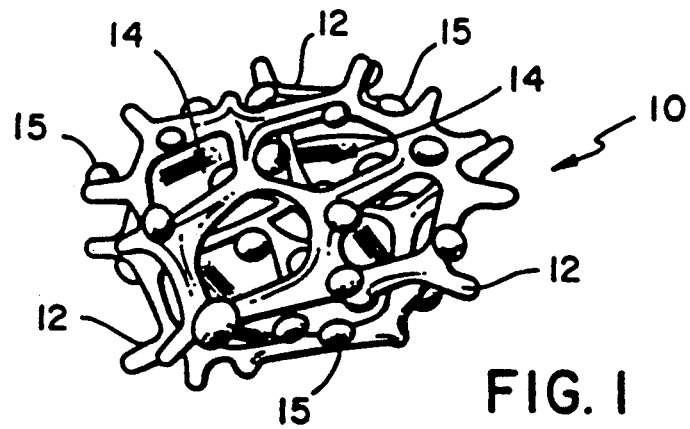
FIG. 1 is a detailed fragmentary diagrammatic view of a portion of composite dispensing material according to the invention showing a reticulated open foam substrate with prepackaged active ingredient particles distributed over and bonded to the webs of the reticulated foam substrate.

A detailed fragmentary diagrammatic view of the composite dispensing material 10 according to the present invention is illustrated in FIG. 1. During foam polymerization of the aqueous phase with the hydrophilic polyurethane prepolymer phase a gas or vapor is generated while the polymer is in the plastic state. Generation of the gas results in formation of bubbles approximately spherical in form. As the bubbles expand, cells are formed of general spherical configuration with optimum packing in which each sphere is surrounded by twelve other spheres. The cells formed by expansion of the gas bubble spheres are generally in the form of dodecahedrons with pentagonal sides or faces. However, throughout the foam mass will be found cells of varying geometry. The walls or faces of the expanding gas bubble spheres are bounded by strands or webs of heavier material. With further expansion a proportion of the cell faces rupture leaving the interconnected webs or strands which form the open foam substrate.

Referring to FIG. 1, the structure of the open foam substrate includes the interconnecting strands, webs, or ligaments 12 surrounding the ruptured faces 14 of the cells formed by expansion of the gas bubble spheres or dodecahedrons during foam polymerization. Distributed over and intimately bonded to the webs of the open foam substrate are the micropackaged active ingredient particles 15, such as for example microcapsules containing an active liquid. Upon rupture or breaking of the microcapsules in response to pressure, abrasion, or other defined environmental stress, the functional liquid or active ingredient is released or expressed and may be readily dispensed from throughout the volume of the composite dispensing material by reason of the open cell or reticulated structure permitting free flow of expressed liquids or ingredients to the surface of the foam for application. Furthermore, following dispensing and application of a functional liquid or ingredient by squeezing or compressing the foam, the excess liquid or other ingredient may be reabsorbed onto the sorbent surfaces of the foam substrate upon its re-expansion.

The hydrophilic characteristics of the open cell polyurethane foam substrate produced by foam polymerization of an aqueous phase with a prepolymer phase is particularly suited for water or aqueous based active liquid and ingredients. Lipophilicity or oil absorbing characteristics may also be imparted to the foam substrate according to the foam polymerization reactants, including for example lipophilic surfactants. A lipophilic composite dispensing material is particularly suited for micropackaged oil base active liquids or functional ingredients.

Figure 2:
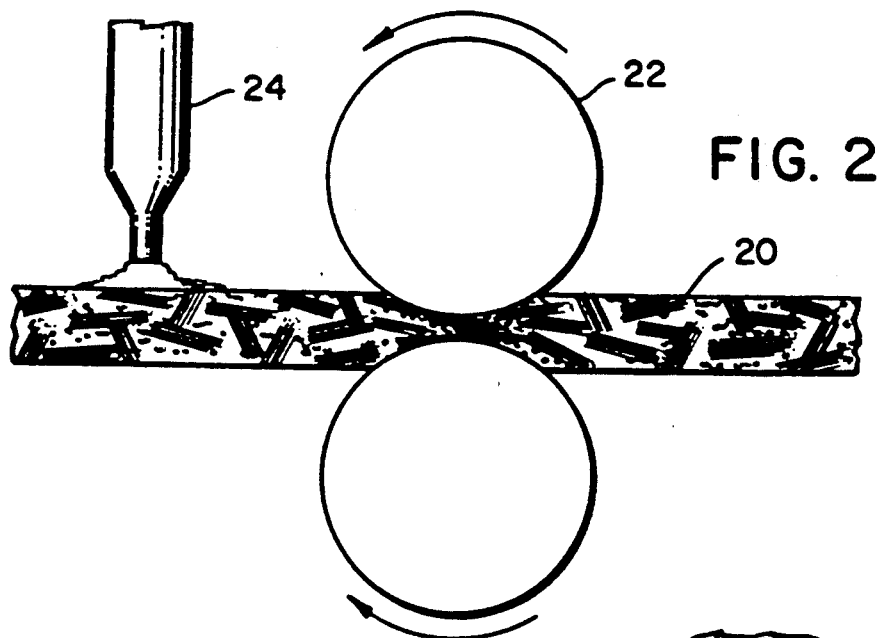
FIG. 2 is a diagrammatic side view of apparatus for forming the composite dispensing material incorporating a fabric skeleton or matrix impregnated with the foam substrate and interpenetrating the foam substrate for example for scrubber, abrasive pad, and washing pad applications.

A process for including a fiber or fabric skeleton or matrix in the composite dispensing material is illustrated in FIG. 2. According to this process, a web or sheet 20 of for example nonwoven fibrous or fabric material with defined thickness or loft is passed between a pair of rollers 22 or other compressing elements. Before passing between the pair of rollers 22 a pourable or flowable mixture 24 of an aqueous phase in the form of a slurry mixture of an aqueous liquid carrier and micropackaged active ingredient particles with a hydrophilic polyurethane prepolymer according to the invention is dispensed or deposited on the web or sheet 20 by dispenser 25 impregnating the sheet or web.

The pair of rollers 22 are set at a defined distance or spacing to achieve a desired density distribution of the polymerizing mixture 24 throughout the skeleton or matrix of the nonwoven sheet 20. Another important factor in determining the density of foam filling the interstices of the nonwoven material is the physical flow rate of the foam polymerizing mixture 24 in relation to the transverse velocity of the nonwoven web 20. These parameters can be adjusted to achieve the desired fill density.

Upon completion of foam polymerization of the mixed aqueous phase and prepolymer phase the open foam substrate interpenetrates the fibrous or fabric skeleton or matrix to the desired density. The open foam substrate fills the interstices of the fibrous or fabric skeleton or matrix with micropackaged active liquid particles distributed over and bonded to the surfaces of the open foam substrate.

Another method for including a nonwoven material matrix or skeleton in the composite dispensing material is during molding of the polymerizing mixture of the aqueous phase and prepolymer phase in a mold. First the mold is filled with the polymerizing mixture. The nonwoven web or matrix is then inserted in the mold. The mold is closed, pressing the composite polymerizing foam mixture through the nonwoven material, filling the spaces and interstices.

The result is in effect a three-phase or three-element composite dispensing material including the fabric skeleton or matrix for example of nonwoven material, the open foam substrate filling the interstices of the skeleton or matrix, and the micropackaged active ingredient particles distributed throughout the composite material and intimately bonded to the open foam substrate. This tough composite material is suitable for a variety of applications including scrubbing, abrasion, and specialized cosmetic applications.

Figure 3:
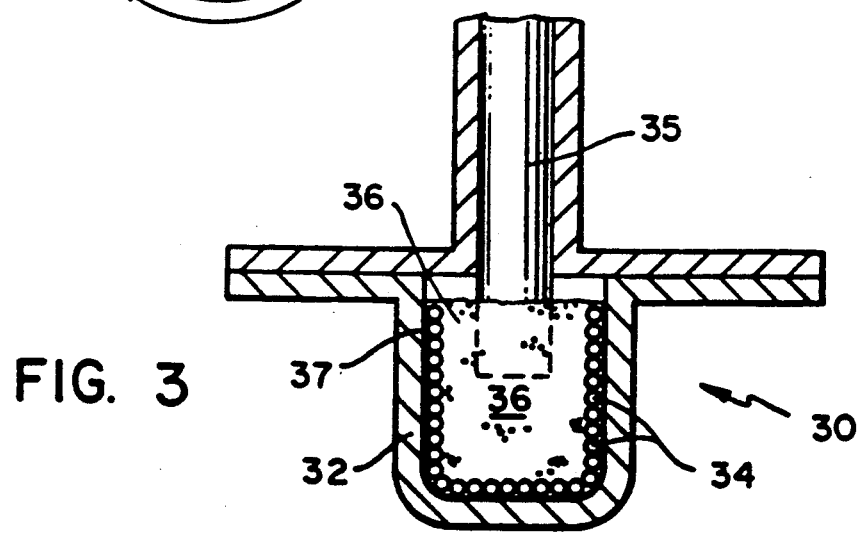
FIG. 3 is a diagrammatic side cross section view of a mold and method for forming an applicator incorporating the composite dispensing material according to the invention.

A further method of forming the composite dispensing material according to the invention is illustrated in FIG. 3 where there is shown a mold 30 defining a molding surface 32. In this example the molding surface 32 is in the shape of an applicator head such as an ear dauber as hereafter described.

According to the method, a layer of micropackaged active ingredient particles 34 is spread over the molding surface 32 and the end of an applicator handle or stick 35 is suspended in the mold. A pourable or flowable foam polymerizing mixture of an aqueous phase comprising an aqueous liquid and a hydrophilic polyurethane prepolymer is poured or deposited in the mold 30. The resulting foam head conforming to the shape of the molding surface forms the applicator head and comprises a soft open foam substrate incorporating the layer of particles 34 in the surface layer of the applicator foam head. The composite dispensing material, according to the invention, thus comprises the exposed surface layer of the applicator head including the surface layer of the open foam substrate and the intimately bonded micropackaged active ingredient particles incorporated into the surface layer of the foam. At the same time the applicator handle or stick 35 is securely bonded to the foam head 36.

In order to adhere the micropackaged active ingredient particles 34 to the surface of the mold, the mold surface is prepared with an adhering film 37, for example petroleum jelly or oil, to provide an adhering surface. The thin film 37 is applied by brushing, spraying, etc. For spraying, petroleum jelly can be prepared in a solvent such as methylene chloride in a ratio of solvent to jelly of, for example, 10/1. The methylene chloride rapidly evaporates, leaving the desired adhering film. The same method can be used in preparing sheet molds with a layer of microencapsulation beads or polymeric lattices for producing composite dispensing material sheets.

A variety of other molding configurations is contemplated by the invention according to the application. For example, the invention provides for molding or foam polymerization of the aqueous phase and prepolymer phase in the form of sheets applied for example over release paper prepared with a layer of micropackaged active ingredient particles spread over the release paper. The release paper is for example treated with release agents such as silicone for release of the molded sheet product incorporating and bonding the particles into the surface layer of the sheet.

EXAMPLE 1

A composite dispensing material was prepared incorporating microencapsulated fragrance. The microencapsulated fragrance was a 40% dispersion or slurry of 1,000 micron capsules in water obtained from QMAX Technology Group, P.O. Box 1509, 125 Bacon Street, Dayton, Ohio, 45402. The microcapsules are purchased and shipped as a dispersion or slurry and the composition of the slurry of 40% particles or capsules by weight and 60% deionized water by weight exhibits the desired pourability and flowability. The water of the microcapsule dispersion or slurry provides the primary aqueous liquid content for the aqueous phase. 76 grams of the microcapsule slurry were mixed with 9.5 grams of American Lecithin HS-3 Surfactant, a cell-size control agent to control foam density and openness of the foam structure. Other surfactants are available to vary the softness of the resulting foam substrate as is well known in the polyurethane foam art. The aqueous phase also included 9.5 grams of Henkel Emulgade 1,000 N1 TM oil soluablizer to impart lipophilic characteristics to the resulting open cell foam.

Both the surfactant and soluablizer constitute a solution of 5% by weight active ingredients in water so that both the soluablizer and surfactant add significantly to the water quantity of the aqueous phase. The aqueous phase also included a pigment, namely 5 grams of Dayglo Company Aurora Red TM pigment to color the resulting composite material bun. The pigment is a 20% solution of active ingredients in water adding further water content to the aqueous phase. As a result, the aqueous phase comprised approximately 68 grams of water and 32 grams of the fragrance microcapsules and the active ingredients of the soluablizer, surfactant, and pigment.

The prepolymer phase was Twin Rivers Engineering TREPOL A62 TM hydrophilic polyurethane prepolymer and the prepolymer was added to the aqueous phase in the ratio of four parts by weight aqueous phase to one part by weight prepolymer phase. The aqueous phase and prepolymer phase were mixed well at room temperature in the range of 65°–75° F. (18°–24° C.) and the mixture was poured into bun molds. After foam polymerization, rising, and setting the buns were removed and demolded in approximately five minutes time. The temperature of the foam polymerization reaction did not exceed approximately 120° F. (49° C.). Excess water from the aqueous phase not consumed in the foam polymerization chemical reaction was removed by evaporation in a conventional air circulating oven at a temperature of approximately 160° F. (71° C.), safely below the rupture temperature or release temperature of the microcapsules. After drying, the payload of active fragrance ingredient contained in the microcapsules distributed and bonded throughout the foam substrate, was expressed by squeezing and reabsorbed by expansion of the foam substrate bun.

The percentage composition by weight of the composite fragrance dispensing material foam bun is summarized in the following Table I.

TABLE I

| Aqueous Phase/Prepolymer Phase Mixture Contents Using 4 pts Aqueous Phase to 1 pt Prepolymer Phase | | | |
|---|---|---|---|
| | % By Weight Of The Total Mixture | % By Weight of Active Ingredient in Each Phase | % By Weight of Active Ingredient In Total Mixture |
| Aqueous Phase | | | |
| Soluablizer | 7.6 | 5 | .38 |
| Surfactant | 7.6 | 5 | .38 |
| Pigment | 4.0 | 20 | .8 |
| Fragrance | 60.8 | 40 | 24.3 |

TABLE I-continued

| Aqueous Phase/Prepolymer Phase Mixture Contents Using 4 pts Aqueous Phase to 1 pt Prepolymer Phase | | | |
|---|---|---|---|
| | % By Weight Of The Total Mixture | % By Weight of Active Ingredient in Each Phase | % By Weight of Active Ingredient In Total Mixture |
| Microcapsules | | | |
| Prepolymer Phase | | | |
| TREPOL A62 Prepolymer | 20.0 | 100 | 20.0 |
| | 100.0% | | 45.86 |

EXAMPLES 2 and 3

Composite dispensing materials molded in the configuration of teddy bears were produced as follows:

91 grams of liquid soap containing 76% water were mixed with 6 grams of chocolate entrapping POLYTRAP TM polymeric lattice network particles, Wickhen Product No. E9235 obtained from Wickhen Products, Inc., Big Pond Road, Huguenot, N.Y., 12746. 5.5 grams of chocolate base pigment were also mixed into the aqueous phase. The 102.5 grams of aqueous phase were mixed with 100 grams of TREPOL A62 TM hydrophilic polyurethane prepolymer and were reacted under time and temperature conditions similar to Example 1 to produce the chocolate entrapping composite dispensing material teddy bears of Example 2.

Example 3 was the same as Example 2 except that the aqueous phase was varied by mixing 91 grams of the liquid soap with 30 grams of Wickhen Product No. E9235 chocolate entrapping polymeric lattice particles and 5.5 grams of chocolate base pigment for delivering, dispensing, or expressing a greater payload of chocolate from the molded teddy bears.

EXAMPLE 4

A nonwoven skeleton or matrix scrubbing pad was produced as follows. The aqueous phase was prepared by mixing 91 grams of liquid soap containing 76% water with 30 grams of Wickhen POLYTRAP 254 TM polymer lattice entrapping particles and 10 grams of Pluronic F88 TM surfactant available from BASF. The 10 grams of F88 surfactant contained the surfactant as a 10% solution in water. The 121 grams of aqueous phase were mixed with 100 grams TREPOL A62 TM prepolymer and dispensed, applied, and flowed on to a ¼"(0.6 cm) thick pink nonwoven sheet 6"×6" (15 cm×15 cm) in area weighing 5.4 grams dry and 22 grams wet. The nonwoven material was a nonwoven polyester fiber having scrubber characteristics and in particular Polyester Nonwoven Serial No. 19083 TM available from Stearns, 100 William Street, Cincinnati, Ohio. The aqueous phase and prepolymer phase mixture was applied in the manner described with reference to FIG. 2 to produce a cleaning pad for releasing active cleaning ingredient from the Wickhen POLYTRAP 254 TM polymer lattice particles bonded to the foam substrate in turn filling the interstices of the nonwoven skeleton or matrix.

EXAMPLE 5

A composite dispensing material was prepared incorporating microencapsulated butyl acetate for nail polish removal. The microencapsulated butyl acetate was a 40% dispersion or slurry of 1,000 capsules or beads in water obtained from QMAX Technology Group. 76 grams of the microcapsule slurry were mixed with 9.5 grams of Emulgade 1,000 N1 TM oil soluablizer, 9.5 grams of American Lecithin HS-3 TM surfactant, and 5 grams of Dayglo base pigment. Both the surfactant and soluablizer were solutions of 5% by weight active ingredients in water and the pigment was a 20% solution of active ingredients in water.

The prepolymer phase was Twin Rivers Engineering TREPOL A62 TM hydrophilic polyurethane prepolymer. 25 grams of the prepolymer was added to 100 grams of the aqueous phase for a ratio of four parts by weight aqueous phase to one part by weight prepolymer phase. The aqueous phase and prepolymer phase were mixed well at room temperature and the mixture was poured into a mold for completion of the polymerization and foaming reaction to produce a sheet of foam 3/32" (0.24 cm) thick. The foam polymerization product was cured in the mold for approximately five minutes and the temperature of the foam polymerization reaction did not exceed approximately 120° F. (49° C.). The mold was open and the sheet was demolded and oven dried for evaporation of excess water in a conventional air circulating oven at a temperature of approximately 150° F. (65.5° C.) for three hours. The sheet was cut into product strips ½" (1.2 cm) wide and 1½" (4.8 cm) long for nail polish removal and related removal applications.

The percentage composition by weight of the composite remover dispensing material foam sheet is summarized in the following Table II.

TABLE II

Aqueous Phase/Prepolymer Phase Mixture Contents
Using 4 pts Aqueous Phase to 1 pt Prepolymer Phase

|  | % By Weight of Aqueous Phase | % By Weight of Total Mixture |
|---|---|---|
| Aqueous Phase | | |
| 40% Dispersion in Water Butyl Acetate Microcapsules | 76 | 60.8 |
| 5% Solution Soluablizer | 9.5 | 7.6 |
| 5% Solution Surfactant | 9.5 | 7.6 |
| 20% Solution Dayglo Base Pigment | 5.0 | 4.0 |
| Prepolymer Phase | | |
| TREPOL A62 Prepolymer | | 20.0 |

While the invention has been described with reference to particular example embodiments, it is intended to cover all variations and equivalents within the scope of the following claims.

I claim:
1. A method for producing a dispensing material comprising:
   spreading a layer of micropackaged active ingredient particles over a molding surface of a mold having a selected applicator configuration;
   preparing an aqueous phase by mixing an aqueous liquid including water and surfactant wetting agent means for adjusting the surface tension of the aqueous phase;
   mixing the aqueous phase with a hydrophilic polyurethane prepolymer phase in ratio by weight of aqueous phase to prepolymer phase of at least approximately 0.02/1 with sufficient excess water in said aqueous phase for cooling the foam polymerization reaction of the aqueous phase and prepolymer phase so that the reaction temperature does not exceed the active ingredient release temperature of the micropackaged active ingredient particles;
   applying the aqueous phase and prepolymer phase mixture over the molding surface and foam polymerizing the mixture in the mold, thereby providing a molded open foam substrate with prepackaged active ingredient particles incorporated and bonded in a surface layer of the molded open foam substrate and with the particles distributed over and bonded to the surfaces of the open foam substrate;
   suspending the end of an applicator handle in the mold during said foam polymerization so that the applicator handle is securely bonded to the molded open foam substrate.

2. The method of claim 1 comprising the step of forming an adhering film over the molding surface for holding the layer of micropackaged active ingredient particles to the molding surface.

3. The method of claim 1, wherein the molding surface and mold comprise an applicator head mold for forming the shape of the dispensing material into an applicator head with the micropackaged active ingredient particles incorporated into the surface layer of the applicator head.

4. The method of claim 1 wherein the micropackaged active ingredient particles are in the granular size range of approximately 400 to 5000 microns.

5. The method of claim 4 wherein the micropackaged active ingredient particles are in the preferred size range of 400 to 1000 microns.

* * * * *